United States Patent [19]

van Aken et al.

[11] 4,427,507
[45] Jan. 24, 1984

[54] PROCESS FOR THE SEPARATION OF GLYCOL FROM AN ELECTROLYTE-CONTAINING AQUEOUS SOLUTION

[75] Inventors: Andreas B. van Aken; Petrus B. J. van Diepen; Jeffrey B. Pedley, all of Amsterdam, Netherlands

[73] Assignee: Shell Oil Company, Houston, Tex.

[21] Appl. No.: 433,065

[22] Filed: Oct. 6, 1982

[30] Foreign Application Priority Data

Mar. 22, 1982 [NL] Netherlands ......................... 8201174

[51] Int. Cl.$^3$ ............................................. B01D 13/02
[52] U.S. Cl. ................................. 204/151; 204/180 P
[58] Field of Search ............................. 204/151, 180 P

[56] References Cited

U.S. PATENT DOCUMENTS 2,865,822  12/1958  Murphy ............................... 204/72
3,192,143   6/1965  Roe ..................................... 204/151
3,779,883  12/1973  Heit ................................. 204/180 P

FOREIGN PATENT DOCUMENTS 1463324  2/1977  United Kingdom .

Primary Examiner—John F. Niebling
Attorney, Agent, or Firm—Ronald R. Reper

[57] ABSTRACT

A process is disclosed for separating glycols from an electrolyte-containing aqueous solution comprises electrodialyzing said solution to increase the glycol to electrolyte content and subsequently removing a substantial part of the water.

5 Claims, No Drawings

PROCESS FOR THE SEPARATION OF GLYCOL FROM AN ELECTROLYTE-CONTAINING AQUEOUS SOLUTION

BACKGROUND OF THE INVENTION

The application relates to a process for the separation of a glycol from an electrolyte-containing aqueous solution.

The application relates in particular to a process for the separation of a glycol from an electrolyte-containing aqueous solution by separating a fraction, the glycol: electrolyte ratio of which has been raised, from the solution by means of a semi-permeable membrane and subsequently recovering the glycol from said fraction. Such a process is known from UK patent specification No. 1463324. It describes how ethylene glycol can be recovered from salt-containing waste water from plants for the preparation of ethylene oxide according to the direct oxidation process by subjecting the waste water charged with salt and glycol to reverse osmosis through a semi-permeable membrane using pressure. According to said process something over 60% of the glycol present in the waste water can be recovered; the remainder has to be either discharged, together with a concentrated salt solution, as a waste stream, or worked-up further at high cost.

It has now surprisingly been found that it is possible to attain a more intensive separation of a glycol from an electrolyte-containing aqueous solution when the solution containing both glycol and electrolyte is subjected to electrodialysis.

SUMMARY OF THE INVENTION

The invention therefore relates to a process for the separation of a glycol from an electrolyte-containing aqueous solution by separating a fraction, the glycol-:electrolyte ratio of which has been raised, from the solution by means of a semi-permeable membrane and subsequently recovering the glycol from said fraction, characterized in that electrodialysis is used to separate said fraction. More particularly the invention provided a process for recovering glycol from an aqueous glycol electrolyte-containing solution comprising introducing said aqueous glycol solution as feed into the depletion compartment of an electrodialytic cell, introducing an electrolyte solution into an anode compartment and a cathode compartment of said electrodialytic cell, said cathode compartment being separated from said depletion compartment by a cation selective membrane, said depletion compartment being separated from the anode compartment by an anion selective membrane, passing a current through said electrodialytic cell and raising the mole ratio of glycol to electrolyte in said aqueous glycol solution in said depletion compartment, and subsequently removing a substantial part of the water from said aqueous glycol solution.

DESCRIPTION OF PREFERRED EMBODIMENTS

Electrodialysis in itself is a known technique of demineralizing aqueous solutions, notably for the production of potable water, but, surprisingly, salt can be removed from mixtures of glycols and water just as effectively without the glycols affecting the process adversely. The glycol content of the aqueous solution may even be 95% or higher. According to the invention at least 80% of the quantity of glycol originally present can be separated and recovered and often even more than 95%.

Glycols are herein defined as alcohols and alkoxy alcohols having two OH groups and so they include, for instance, ethylene glycol (1,2-ethanediol), propylene glycol (1,2 propanediol), trimethylene glycol (1,3-propanediol), diethylene glycol ($HOC_2H_4OC_2H_4OH$) and triethylene glycol ($HOC_2H_4OC_2H_4OC_2H_4OH$). Glycols are reasonably soluble in water, and glycols having fewer than seven carbon atoms are even readily soluble in water.

Electrodialysis is a method which—in short—utilizes the selective transfer of ions through membranes due to a difference in potential having been applied. Since some membranes allow passage almost exclusively to cations (cation-selective membranes) and other membranes almost exclusively to anions (anion-selective membranes), the ion concentration in certain solutions may be raised or reduced. When an array of alternating anion-selective and cation-selective membranes is placed in a direct voltage electric field, the solution enclosed by one pair of membranes is diluted (the diluate) and the solution enclosed by the adjacent pair of membranes becomes more concentrated (the concentrate).

Any material that is used for carrying out electrodialysis in practice is eligible as membrane material. A useful survey of such materials and of practical embodiments of electrodialysis units is given in, for instance, "Industrial Processing with Membranes", edited by R. E. Lacey and S. Loeb, Wiley-Interscience, New York, 1972, pp. 6–7. However, it has been found that exceptionally good results are achieved when, what is called "tight-pore membranes" are used instead of the more or less conventional membrane materials.

The more or less conventional membranes allow more water molecules to be transferred through the membrane per quantity of electric charge passed through than the tight-pore membranes. The phenomenon of simultaneous water transfer is called electroosmotic flux. Accordingly, as this flux is lower, the concentrate will have a higher concentration.

In actual practice anionselective membranes with an electroosmotic flux of from about 115 to 200 gram (water)/Faraday (electric charge transferred) (g/F) are called conventional membranes and anionselective membranes with an electroosmotic flux of less than about 115 g/F are called membranes of the tight-pore type. For cation-selective membranes these values are somewhat higher: those with an electroosmotic flux of from about 210 to 300 g/F are called conventional membranes and so, those with a value lower than about 210 g/F are called membranes of the tight-pore type. The sum of the electroosmotic fluxes of a single tight-pore cell pair—viz. one tight-pore anion-selective membrane and one tight-pore cation-selective membrane—is usually less than 300 g/F; values below 200 g/F have not yet proven feasible. Thus, preference is given to the use of electrodialysis cell pairs the sum of whose electroosmotic fluxes is less than 300 g/F.

Tight-pore membranes have the additional, unexpected advantage of allowing easier passage to water than to glycol, in other words: the glycol concentration is lower in the electroosmotic flux than in the feed supplied. In conventional membranes, however, it is seen that the ratio in which glycol and water are transferred through the membrane is the same as the ratio in which they were present in the feed. Thus, the effectiveness of the glycol separation is enhanced by the use of tight-pore membranes.

Usually, the direct voltage applied between the anode and the cathode advantageously lies in the range between 0 and 4.5 Volt and is preferably in the range of from about 1.5 to about 2.5 V, particularly about 2 V. Depending on electrolyte concentration and type of ions and thus, depending on the current density, this voltage may be set somewhat higher or lower by techniques known to those skilled in the art.

Subsequent to electrodialysis a substantial part of the water may be removed by any convenient process employing heat and/or vacuum such as flashing, evaporation and the like.

The process according to the invention is particularly suitable for use in recovering glycol from a typical waste stream found in an ethylene oxide plant.

In the preparation of ethylene oxide according to the direct oxidation process carbon dioxide and water are formed in a side reaction $$C_2H_4 + 3O_2 \rightarrow 2CO_2 + 2H_2O$$

and also, to a minor extent, organic acids, such as formic acid, which are neutralized with a base and discharged together with the water. At the same time (alkali metal) (bi)carbonate is formed. The salt solution thus obtained also contains ethylene glycol and diethylene glycol which are formed by hydrolysis of ethylene oxide diisolved in the water. Whereas the ethylene oxide which, moreover, is present in the salt solution is easy to remove by distillation, the glycols together with the salt, remain behind in the water that leaves the plant as a stream of waste water which, although containing relatively small quantities of organic matter, is nevertheless highly charged with electrolyte.

The overall concentration of glycols and salt present in this waste water varies within the range of from 1.5 to 8% w. The organic charge causes high processing costs in biological purifiers on the one hand and loss of glycol amounting to about 0.5% of the production of ethylene oxide on the other hand. It is therefore desirable to recover glycol present in this waste water, which, according to the invention, has now become surprisingly simple. The application therefore also relates to a process for the preparation of ethylene oxide by way of direc oxidation, characterized in that the process according to the invention is used to separate the glycols formed in salt-containing waste water through hydrolysis of ethylene oxide.

Another use is found in the dewatering of natural gas by using glycol, for instance immediately after winning, being produced, or during transport through pipelines. When gas is produced at a reservoir, water, and hence also some dissolved salt—mainly NaCl—becomes entrained. The gas is then dried by absorption in a glycol, notably triethylene glycol. In the subsequent regeneration of this glycol—for instance in a vacuum regenerator—salt deposits cause problems. These problems may be overcome by treating the glycol-water mixture according to the process of the invention, and thus separating a small bleed of concentrated salt solution from the bigger stream of glycol and water which can then be fed to the vacuum regenerator. The application therefore also relates to a process for drying natural gas-containing saline water by using a glycol in which the glycol is regenerated after absorption of the saline water, characterized in that in the regeneration process the glycol is separated using the process according to the invention.

As a third option for use the application also relates to a process for the preparation of $C_{10}$–$C_{20}$ alpha-olefins by way of oligomerization of ethene using a catalyst dissolved in butane-diol, characterized in that salt-contaminated butanediol is worked-up to be recirculated using the process according to the invention. A further description of this process for the preparation of olefins may be found in the article published by E. R. Freitas and C. R. Gum in Chemical Engineering Progress (January, 1979), pp. 73–76.

Finally, the process according to the invention might also be used in the regeneration of glycol-water antifreeze mixutres, for instance for motor car engines.

The invention is now further elucidated with the aid of the following examples.

EXAMPLES

A number of experiments were carried out with glycol-water mixtures from an ethylene oxide plant. The salt consisted about 90% of HCOONa, sodium formate, and about 10% of $Na_2CO_3$, sodium carbonate, and the greater part of the glycol consisted of ethylene glycol and the remainder of oligo-condensates, mainly diethylene glycol—depending on the glycol:water ratio. Since the various glycols show but negligibly small differences in their membrane transfer rates (electroosmotic flux), "glycol" will hereinafter be mentioned as a collective concept, no exact compositions being stated.

The electrodialysis unit used was what is called the "Stack Pack" laboratory unit of "Ionics Corporated", whose hydrodynamic design is such that the results obtained therein can be converted instantly to those of bigger units. All the experiments were carried out at 25° C. The effective membrane area was 0.176 $m^2$ both when conventional membranes and tight-pore membranes were used. The glycol contents of the solutions were determined by gas chromatography, and the Na contents were determined by atomic absorption spectroscopy.

EXAMPLE 1

A 5.47 kg sample of solution having a glycol content of 4.8% w and a Na content of 3520 ppmw was introduced into one inlet of the electrodialysis unit as the stream to be desalted (diluate-in), while a quantity of 1.37 kg of demineralized water having a Na content of 80 ppmw was introduced into the other inlet (concentrate-in). In the electrodialysis unit dilution and concentration of salt and glycol were brought about through the effect of a voltage of 3.0 Volt/cell pair (diluate-out and concentrate-out, resp.). In the electrodialysis conventionl membranes were used, namely as anion-selective membrane having an electroosmotic water transfer of 145 g/F (Ionics Inc. code number 103 PZL 386) and a cation-selective membrane having an electroosmotic water transfer of 240 g/F (Ionics Inc. code number 61 AZL 386). Further data and the results are given in Table I.

EXAMPLE 2

A sample from another stream from the ethylene oxide plant containing less water and more glycol was treated in a way analogous to that of Example 1. The data and results are also shown in Table I.

EXAMPLE 3

The conventional membranes were replaced by tight-pore membranes, namely Ionics Inc. code number 204 UZL 386 (anion-selective, electroosmotic flux 85 g/F) and Ionics Inc. code number 61 CZL 386 (cation-selective, electroosmotic flux 180 g/F). Further experimental data and the results are given in Table I.

TABLE I

| Example | | 1 | | 2 | | 3 | | comparison | |
|---|---|---|---|---|---|---|---|---|---|
| glycol content | | low | | high | | low | | | |
| voltage/ | | | | | | | | | |
| cell pair | V | 3.0 | | 4.0 | | 2.0 | | reverse osmosis | |
| time | $10^3$ sec | 1.86 | | 2.46 | | 2.40 | | at 30 atm. | |
| overallcharge | $10^3$ A.s | 9.42 | | 11.62 | | 5.69 | | | |
| | | in | out | in | out | in | out | feed | pure product |
| diluate | kg | 5.47 | 5.24 | 5.30 | 5.03 | 6.07 | 5.96 | 700 | 521 |
| glycol | % w. | 4.8 | 3.9 | 55.3 | 56.2 | 16.4 | 16.2 | 1.5 | 1.28 |
| sodium | ppm w | 3520 | 145 | 4700 | 1300 | 1630 | 108 | 12000 | 500 |
| | | | | | | | | | residue |
| concentrate | kg | 1.37 | 1.60 | 0.86 | 1.10 | 0.90 | 1.01 | — | 179 |
| glycol | % w. | — | 0.8 | — | 9.88 | 1.09 | 1.92 | — | 2.13 |
| sodium | ppm w | 80 | 12300 | 180 | 17100 | 147 | 9250 | — | 45600 |
| Salt removal % | | | 96 | | 74 | | 93 | | 97 |
| glycol retention % | | | 78 | | 96 | | 97 | | 63 |
| type of membrane | | conventional | | | | tight-pore | | polyamide | |

N.B. salt removal = $\frac{\text{sodium in "diluate in"} - \text{sodium in "diluate-out"}}{\text{sodium in "diluate in"}} \frac{kg}{kg} \times 100\%$ glycol retention = $\frac{\text{glycol in "diluate out"}}{\text{glycol in "diluate in"}} \frac{kg}{kg} \times 100\%$

COMPARATIVE EXAMPLE

For comparison the data of a process for the recovery of glycol using reverse osmosis as described in UK Patent Specification 1463324 have been included in Table I.

As is seen from the figures, both electrodialysis and reverse osmosis can be used to remove a considerable percentage of the salt, but the use of electrodialysis allows much more glycol to be recovered: for instance 97%, using electrodialysis; for instance 63%, using reverse osmosis.

In addition, it becomes apparent that the tight-pore membranes yield the best results for glycol retention and salt removal together.

We claim;

1. In a process for recovering a glycol having two OH groups from an aqueous glycol electrolyte-containing solution comprising introducing said aqueous glycol solution as feed into the depletion compartment of an electrodialytic cell, introducing an electrolyte solution into an anode compartment and a cathode compartment of said electrodialytic cell, said cathode compartment being separated from said depletion compartment by a cation selective membrane, said depletion compartment being separated from the anode compartment by an anion selective membrane, passing a current through said electrodialytic cell at a direct voltage in the range between 0 and 4.5 volt and raising the mole ratio of glycol to electrolyte in said aqueous glycol solution in said depletion compartment, and subsequently removing a substantial part of the water from said aqueous glycol solution, the improvement comprising that in the electrodialysis cell membrane pairs are used the sum of whose electroosmotic fluxes is less than 300 g/F.

2. A process as in claim 1, wherein the current is passed at a direct voltage in the range between 1.5 to about 2.5 Volt.

3. A process as in claim 1 wherein said feed is salt-containing waste water containing glycols formed by hydrolysis of ethylene oxide.

4. A process as in claim 1 wherein said feed is glycol-containing saline water from a process for drying natural gas.

5. A process as in claim 1 wherein said feed is salt-contaminated butanediol originating from a process for the preparation of $C_{10}$–$C_{20}$ alpha-olefins by way of oligomerization of ethene using a catalyst dissolved in butanediol.

* * * * *